US009879289B2

(12) United States Patent
Karau et al.

(10) Patent No.: US 9,879,289 B2
(45) Date of Patent: Jan. 30, 2018

(54) METHOD FOR THE PREPARATION OF 2-KETO CARBOXYLIC ACID

(75) Inventors: Andreas Karau, Vieux Moulin (FR); Nicolas Morin, Venette (FR); Robert Gerstmeir, Werther (DE)

(73) Assignee: Evonik Degussa GmbH, Essen (DE)

( * ) Notice: Subject to any disclaimer, the term of this patent is extended or adjusted under 35 U.S.C. 154(b) by 1181 days.

(21) Appl. No.: 13/321,295

(22) PCT Filed: May 10, 2010

(86) PCT No.: PCT/EP2010/056345
§ 371 (c)(1), (2), (4) Date: Nov. 18, 2011

(87) PCT Pub. No.: WO2010/139527
PCT Pub. Date: Dec. 9, 2010

(65) Prior Publication Data
US 2012/0065428 A1    Mar. 15, 2012

(30) Foreign Application Priority Data
Jun. 5, 2009 (EP) .................................. 09162079

(51) Int. Cl.
*C12P 7/40* (2006.01)
*C12P 7/26* (2006.01)

(52) U.S. Cl.
CPC .. *C12P 7/26* (2013.01); *C12P 7/40* (2013.01)

(58) Field of Classification Search
CPC .............................................. C12P 7/40
USPC ............................................... 435/136
See application file for complete search history.

(56) References Cited

U.S. PATENT DOCUMENTS

| | | | | |
|---|---|---|---|---|
| 6,288,275 | B1 * | 9/2001 | Turner | ............................ 562/593 |
| 7,632,663 | B1 | 12/2009 | Eggeling et al. | |
| 2010/0280123 | A1 | 11/2010 | Karau et al. | |

FOREIGN PATENT DOCUMENTS

| | | |
|---|---|---|
| EP | 1 767 616 | 3/2007 |
| EP | 1 767 616 A2 | 3/2007 |
| EP | 1767616 A2 * | 3/2007 |
| JP | 52 108086 | 9/1977 |
| JP | S52-108086 A | 9/1977 |
| JP | 55 042550 | 3/1980 |
| JP | S55-042550 A | 3/1980 |
| JP | 2002-537771 | 11/2002 |
| WO | 2006 082252 | 8/2006 |
| WO | 2006/082252 A2 | 8/2006 |
| WO | 2006/082252 A3 | 8/2006 |
| WO | WO 2006082252 A2 * | 8/2006 |
| WO | 2006/082252 A3 | 12/2006 |
| WO | WO 2008/122473 A2 | 10/2008 |
| WO | WO 2008/122613 A2 | 10/2008 |

OTHER PUBLICATIONS

Machine translation of EPO Patent Document No. EP 1767616 A2 by Blombach et al., obtained Jul. 10, 2015.*
Meister, A. Methods Enzymol. 1957, 3, 404-414.*
Ohmori et al. Journal of Membrane Science 2000, 171, 263-271.*
Hermann, T. Journal of Biotechnology 2003, 104, 155-172.*
Morbach et al. Appl. Microbiol. Biotechnol. 1996, 45, 612-620.*
Krause et al. Applied and Environmental Microbiology 2010, 76, 8053-8061.*
Zahoor et al. Computational and Structural Biotechnology Journal, 2012, 4, 1-11.*
Tabuchi, T., "Organic acid fermentation by yeasts. VIII. Accumulation of alpha-ketoisocaproic acid from glucose in cultures of yeasts," Nippon Nogei Kagaku Kaishi, vol. 47, No. 10, pp. 611-615, (1973) XP002614533 (English abstract only).
Wagner, R. P., et al., "The Accumulation of Keto Acids and Acetaldehyde by a Strain of Neuro-Spora Inhibited by Threonine," Journal of Biological Chemistry, vol. 216, pp. 251-262, (1955) XP002614536.
Pospisil, S., et al., "Overproduction of 2-ketoisovalerate and monensin production by regulatory mutants of Streptomyces cinnamonensis resistant to 2-ketobutyrate and amino acids," FEMS Microbiology Letters, vol. 172, No. 2, pp. 197-204, (1999) XP002614537.
Beck, H. C., et al., "Catabolism of leucine to branched-chain fatty acids in *Staphylococcus xylosus*," Journal of Applied Microbiology, vol. 96, No. 5, pp. 1185-1193, (2004) XP002614538.
International Search Report dated Dec. 30, 2010 in PCT/EP10/056345 Filed May 10, 2010.
Decision of Refusal dated Sep. 7, 2015 issued in corresponding Japanese patent application No. 2012-513529.
Colowick et al.—"Methods in Enzymology", 1957, vol. 3, pp. 404-414.
Wagner et al.—"The Accumulation of Keto Acids and Acetaldehyde by a Strain of Neurospora Inhibited by Threonine", Journal of Biological Chemistry, 1955, vol. 216, pp. 251-262.
Pospisil et al.—"Overproduction of 2-ketoisovalerate and monensin production by regulatory mutants of *Streptomyces cinnamonensis* resistant to 2-ketobutyrate and amino acids", FEMS Microbiology Letters 172 (1999), pp. 197-204.
Tabuchi—"Accumulation of α-Ketoisocaproic Acid from Glucose in Cultures of Yeasts", Nippon Nogei Kagaku Kaishi, 1973, vol. 47, No. 10, pp. 611-615 (with English Abstract).
Hüser et al.—"Rational Design of a *Corynebacterium glutamicum* Pantothenate Production Strain and Its Characterization by Metabolic Flux Analysis and Genome-Wide Transcriptional Profiling", Applied and Environmental Microbiology, Jun. 2005, pp. 3255-3268, vol. 71, No. 69.

(Continued)

*Primary Examiner* — Matthew P Coughlin
(74) *Attorney, Agent, or Firm* — Oblon, McClelland, Maier & Neustadt, L.L.P.

(57) ABSTRACT

The present invention refers to a method for the preparation of 2-keto carboxylic acid having the general formula $R^1$—CO—COOH, wherein $R^1$ is a branched alkyl group having 3 to 7 carbon atoms, or a salt thereof, comprising a fermentation step wherein a microorganism is grown in a culture medium in order to provide a culture broth containing 2-keto carboxylic acid or a salt thereof.

20 Claims, No Drawings

(56) References Cited

OTHER PUBLICATIONS

Sahm et al.—"D-Pantothenate Synthesis in *Corynebacterium glutamicum* and Use of panBC and Genes Encoding L-Valine Synthesis for D-Pantothenate Overproduction", Applied and Environmental Microbiology, May 1999, pp. 1973-1979, vol. 65, No. 5.
Morbach et al.—"Engineering the homoserine dehydrogenase and threonine dehydratase control points to analyse flux towards L-isoleucine in *Corynebacterium glutamicum*", Applied Microbiology Biotechnology, 1996, 45, pp. 612-620.

* cited by examiner

METHOD FOR THE PREPARATION OF 2-KETO CARBOXYLIC ACID

The present invention refers to a method for preparing 2-keto carboxylic acid, particularly 2-ketoisovaleric acid, 2-keto-4-methylpentane acid, and/or 2-keto-3-methylpentane acid using a fermentation step.

2-keto carboxylic acids are useful compounds in pharmacy and are used for synthesis of herbicides and fungicides. 2-keto carboxylic acids are known to reduce the level of LDL cholesterol, triglycerides and free radicals in blood plasma. Particularly 2-ketoisovaleric acid is used as food supplement for renal failure patients.

It is known in the state of art to prepare 2-keto carboxylic acids, for example 2-ketoisovalerate, by chemical synthesis. For example, the preparation of 2-ketoisovalerate by chemical synthesis is carried out in two steps, by oxidation of the respective 2-hydroxy isovaleric acid ethylester using $CrO_3$, and subsequent saponification of the ester in order to yield 2-ketoisovalerate. This process involves the drawback of using high temperatures, toxic $CrO_3$ and diverse environmentally hazardous solvents.

In biosynthesis 2-keto carboxylic acid is the direct precursor for the respective amino acid: for example 2-ketoisovalerate is the direct precursor of the amino acid valine. In microorganisms 2-ketoisovalerate is produced in the cell and excreted into the culture medium. 2-keto acids are described in the prior art to be used as precursor for the preparation of the respective amino acid by fermentation (GB 2,161,159; GB 2,147,579).

Although it is known in the literature that microorganisms produce 2-keto carboxylic acids, for example 2-ketoisovalerate, methods for preparing and isolating 2-keto carboxylic acids at high purities by using fermentation have not been described so far but 2-keto carboxylic acids were mentioned only as intermediate products or educts for the preparation of amino acids.

Problem and Solution

The object of the present invention was to provide a method for the preparation of 2-keto carboxylic acids, in particular 2-ketoisovalerate, 2-keto-4-methylpentane acid, and/or 2-keto-3-methylpentane acid, which avoids the drawbacks of chemical synthesis.

The problem is solved by a method for the preparation of 2-keto carboxylic acid having the general formula (I) $R^1$—CO—COOH, wherein $R^1$ is a branched alkyl group having 3 to 7 carbon atoms, or a salt thereof, comprising the following steps:
a) a fermentation step wherein a microorganism is grown in a culture medium in order to provide a culture broth containing 2-keto carboxylic acid or a salt thereof;
b) subjecting the fermentation broth obtained in step a) to one or more steps chosen from the group consisting of ion exchange, extraction process, distillation process In a preferred embodiment of the invention the process comprises the following steps:
a) a fermentation step wherein a microorganism is grown in a culture medium in order to provide a culture broth containing 2-keto carboxylic acid or a salt thereof;
b) subjecting the fermentation broth obtained in step a) to ion exchange.
c) preferably subjecting the effluent obtained in step b) to one or more further purification step chosen from the group consisting of ion exchange, extraction or distillation;
d) preferably subjecting the product obtained in step c) to a further concentration, precipitation or crystallization step or combination thereof and obtaining 2-keto carboxylic acid or a salt thereof.

In a preferred embodiment of the invention the process comprises the following steps:
a) a fermentation step wherein a microorganism is grown in a culture medium in order to provide a culture broth containing 2-keto carboxylic acid or a salt thereof;
b) subjecting the fermentation broth obtained in step a) only to a distillative process (steam distillation with water addition until full impoverishment of the sump), after initial pH-shift (acidification to pH 1) of the fermentation broth.

This embodiment avoids the use of ion exchange treatment. Surprisingly with this step the Keto-acids could be removed quite selectively from the fermentation broth and other organic acids did stay in the distillation sump.

In a preferred method the 2-keto carboxylic acid is a compound having the general formula $R^1$—CO—COOH, wherein $R^1$ is a branched alkyl group having 3, 4 or 5 carbon atoms, or a salt thereof.

Further preferred, $R^1$ is selected from the group consisting of isopropyl, isobutyl, sec.-butyl, tert.-butyl, 2-methyl-butyl, 3-methylbutyl. Even further preferred $R^1$ is selected from the group consisting of isopropyl, isobutyl, sec.-butyl.

In a particularly preferred method the 2-keto carboxylic acid is 2-ketoisovaleric acid or a salt thereof.

In a further preferred embodiment of the present invention the culture broth obtained in step a) contains at least 10 g/l, preferably at least 15 g/l and further preferred at least 20 g/l and most preferred at least 40 g/l 2-keto carboxylic acid, preferably 2-ketoisovaleric acid, or a salt thereof.

It is further preferred that the microorganism used for the fermentation step has an improved capability to produce a compound of formula (I), preferably a compound selected from the group consisting of 2-ketoisovaleric acid, 2-keto-4-methylpentane acid, and 2-keto-3-methylpentane acid or a mixture thereof.

Preferably, the microorganism used for the fermentation step is *Corynebacterium* with increased ability to produce 2-ketoisovaleric acid, 2-keto-4-methylpentane acid, and/or 2-keto-3-methylpentane acid, particularly preferred *Corynebacterium glutamicum*. It is particularly useful to use a *Corynebacterium* strain which is reduced or deficient in one or more proteins like transaminase B (E.C. 2.6.1.42, endoded by the ilvE-gene), valine-pyruvat transaminase AvtA (E.C. 2.6.1.66, encoded by the avtA-gene) or alanine transaminase (E.C. 2.6.1.2, encoded by the alaT-gene). In addition it is useful to use a *Corynebacterium* strain which is reduced or deficient in one or more proteins like the E1 subunit of pyruvate dehydrogenase (E.C. 1.2.4.1, encoded by the aceE gene), pyruvate quinone oxidoreductase (E.C. 1.2.2.2, encoded by the pqo gene), phosphogluco isomerase (E.C. 5.3.1.9, encoded by the pgi gene). In order to achieve a good yield the *Corynebacterium* strain is reduced or deficient in some, all or combinations of the mentioned gene products. The gene product of aceE catalyses the reaction of pyruvate to acetyl CoA. The gene product of ilvE catalyses the transamination of 2-ketoisovaleric acid to the amino acid valine (which converts one mol glutamate to alpha-ketoglutarate per transamination reaction). The gene product of avtA catalyses the transamination of 2-ketoisovaleric acid to the amino acid valine (which converts one mol alanine to pyruvate per transamination reaction). The gene product of the alaT gene catalyses the reaction from pyruvate to alanine. The gene product of pqo catalyses the reaction from pyruvate to acetate. The gene product of pgi catalyses the reaction from glucose-6-phosphate to fructose-6-phosphate.

In addition, the *Corynebacterium* strain may overexpress any one or more or all of the following preferably endogenous genes ilvBN (gene encoding acetohydroxyacid synthase, E.C. 4.1.3.18), ilvC (gene encoding acetohydroxyacid isomeroreductase, E.C. 1.1.1.86) and ilvD (gene encoding dihydroxyacid dehydratase, E.C. 4.2.1.9). The ilvBN, ilvC and ilvD genes encode the enzymes which represent the metabolic pathway from pyruvate to 2-ketoisovaleric acid. For ketomethylvalerate production, *Corynebacterium* strains may also overexpress any one or more or all of the following preferably endogenous genes ilvA (gene encoding threonine dehydratase, E.C. 4.2.1.16), hom (gene encoding homoserine dehydrogenase, E.C. 1.1.1.3), thrB (gene encoding homoserine kinase, E.C. 2.7.1.39), thrC (gene encoding threonine synthase, E.C. 4.2.3.1), lysC (gene encoding aspartokinase, E.C. 2.7.2.4), aspartate aminotransferase (aat, E.C. 2.6.1.1), aspartate semialdehyse dehydrogenase (asd, E.C. 1.2.1.11), pyruvate carboxylase (pyc, E.C. 6.4.1.1). For ketoisocaproate production, *Corynebacterium* strains may also overexpress any one or more or all of the following preferably endogenous genes leuA (gene encoding 2-isopropylmalate synthase (E.C. 2.3.3.13) leuB (3-isopropylmalate dehydrogenase, E.C. 1.1.1.85), leuCD (3-isopropylmalate dehydratase, E.C. 4.2.1.33).

In a particularly preferred embodiment the strain *Corynebacterium* has the genotype Δ-aceE, Δ-ilvE and overexpresses the genes ilvBN, ilvC and ilvD and is used for the preparation of 2-ketoisovaleric acid.

Besides *Corynebacterium* other bacterial strains, yeasts as well as fungal microorganisms can be used for the fermentation process of the present invention, such as *Escherichia coli, Bacillus, Brevibacterium, Pseudomonas, Streptomyces*.

In a further preferred embodiment, before the culture broth is applied to the ion exchange step (b) an additional step of removal of cells and/or cell debris from the culture broth is carried out, wherein this removal is carried out preferably by filtration, centrifugation or sedimentation or by a combination of said methods.

Recombinant techniques are known to skilled man from the state of art. The following table contains the accession numbers of used genes.

TABLE

| Accession number of the genes | | |
|---|---|---|
| Gene name | Gene ID | Accession Number (NCBI) |
| aceE | 3344029 | NC_006958.1 |
| ilvE | 3344782 | NC_006958.1 |
| alaT | 3342681 | NC_006958.1 |
| avtA | 3344823 | NC_006958.1 |
| pqo (Synonym poxB) | 3344335 | NC_006958.1 |
| ilvB | 3345149 | NC_006958.1 |
| ilvN (Synonym ilvH) | 3343142 | NC_006958.1 |
| ilvC | 3343961 | NC_006958.1 |
| ilvD | 3344114 | NC_006958.1 |
| ilvA | 3342699 | NC_006958.1 |
| thrB | 3345034 | NC_006958.1 |
| thrC | 3342939 | NC_006958.1 |
| hom | 3343957 | NC_006958.1 |
| lysC | 3345161 | NC_006958.1 |
| aat (Synonym aspB) | 3343262 | NC_006958.1 |
| asd | 3345564 | NC_006958.1 |
| Pyc | 3344537 | NC_006958.1 |

TABLE-continued

| Accession number of the genes | | |
|---|---|---|
| Gene name | Gene ID | Accession Number (NCBI) |
| leuA | 3344881 | NC_006958.1 |
| leuC | 3345229 | NC_006958.1 |
| leuD | 3345257 | NC_006958.1 |
| leuB | 3345533 | NC_006958.1 |

In addition, after removal of cells and/or cell debris from the culture broth and before step b) a pre-purification may be carried out by using ion exchange resin or charcoal.

In a preferred embodiment of the method in step b) a cationic resin is used for the ion exchange step. This step is used for removing amino acids and cations. Preferably, the cationic resin comprises a strongly acidic exchange resin having a sulfonic functionality, i.e. a resin comprising sulfonic acid groups.

In a further preferred embodiment, in step c) for ion exchange an anionic resin is used. This step is used for removing acids other than 2-keto carboxylic acids (2-oxo-carboxylic acids). Preferably, the anionic resin comprises a weak basic exchange resin having an amine functionality. The desired product preferably is eluted from the anionic resin with a strong acid, preferably hydrochloric acid. Further preferred, the molarity of said acid for elution from the anionic resin is between 0.1 N and 4 N, still further preferred 1 N to 3 N and most preferred 2.5 N to 3 N.

In an alternative embodiment, in step c) a distillation is carried out, preferably a steam distillation. Further preferred, the distillation is carried out at a temperature from 10 to 85° C., still further preferred from 20 to 75° C., even further preferred from 25 to 70° C. and particularly preferred from 35 to 65° C.

In a further preferred embodiment the initial solution subjected to distillation has a pH of 1 to 10, preferably 1 to 2.

The distillation is preferably carried out at a pressure from 10 to 100 mbar, further preferred from 20 to 80 mbar, still further preferred from 20 to 65 mbar, and particularly preferred from 20 to 25 mbar.

In a further preferred method of the present invention in step d) of the precipitation and crystallization step the 2-keto carboxylic acid is obtained as salt selected from the group consisting of $Ca^{2+}$, $Mg^{2+}$, $Na^+$, $K^+$ or as salt with an amino acid. It is particularly preferred that the pH of the solution is set to 5.0 to 6.0, preferably of 5.5 to 6.0, preferably by the addition of $CaCO_3$. Subsequently, the solution is concentrated under reduced pressure.

Preferably, the purity of the 2-keto carboxylic acid or its salt achieved by the method of the present invention is 60% by weight or more, further preferred 80% by weight or more, most preferred 90% or more.

Further preferred a global yield of 2-keto carboxylic acid, preferably of 2-ketoisovalerate, of at least 50% by weight is achieved.

In a further preferred embodiment the culture medium for fermentation contains as carbon source renewable raw materials, preferably selected from the group glucose, saccharose.

The present invention also provides a 2-keto carboxylic acid having the general formula (I) $R^1$—CO—COOH, wherein $R^1$ is a branched alkyl group having 3 to 7 carbon atoms, or a salt thereof, preferably 2-ketoisovaleric acid or a salt thereof, with a purity greater than 60% by weight, preferably greater than 80% by weight particularly preferred greater than 90% by weight obtained from by the method according to the present invention as described above.

EXAMPLES

Example 1

Preparation of 2-ketoisovalerate (i) Ion Exchange, (ii) Distillation)

A *Corynebacterium glutamicum* strain having the genotype Δ-aceE, Δ-ilvE and which overexpresses the genes ilvBN, ilvC and ilvD was cultured in shake flasks with LB media until the stationary phase was reached. The culture medium contained a carbon source and nitrogen source. The culture broth was centrifuged in order to remove cells and cell debris. The supernatant of the culture broth had a pH of 6.7 and contained 5 g/l 2-ketoisovalerate.

Subsequently, the supernatant was percolated on a strong cationic resin (Amberlite FPC 22Na) in order to remove amino acids and cations (mainly $Na^+$). For this step 350 ml resin volume was used per 1000 ml culture broth (supernatant). Then the resin was washed with 1 volume $H_2O$ and the effluent fraction was collected until a Brix (measure of the concentration of dissolved solids —as sugars—per hundred parts aqueous solution, by a refractometer) of below 0.1 was reached.

The effluent having a Brix of 7 was concentrated on a Büchi evaporator at a temperature of 60° C. and a pressure of 20-25 mbar. The receipts were collected until no further distillation occurred and an oily residue was obtained. The oily residue was added with $H_2O$ and the concentration was continued until no more distillation occurred. This step was repeated as many times until the associated distillation receipt had an overall Brix below 0.1.

Subsequently all receipts from the distillation were pooled and $CaCO_3$ was added until pH 5.5 to 6.0 was reached. The solution was decoloured for 1 to 5 hours using 2 wt. -% active charcoal per weight 2-ketoisovalerate. Then the solution was filtered through a 0.45 μm membrane in order to remove the charcoal.

The filtrate was concentrated on a Büchi evaporator at a temperature of 40-45° C. and a pressure of 20-25 mbar until a suspension of crystals was obtained. The suspension was cooled slowly down to 20° C. and after at least 1 hour at 20° C. the crystals were filtered on a glass funnel and washed with $H_2O$.

The wet cake was dried under vacuum at a temperature of 40-45° C. until constant weight was reached and subsequently analysed as $Ca^{2+}$ salt of 2-ketoisovalerate. Analysis by HPLC revealed a purity of said 2-ketoisovalerate salt of greater than 90% by weight (see table 1).

TABLE 1

Purity of 2-ketoisovalerate obtained according to example 1

| Compound | amount [% by area] |
| --- | --- |
| 2-ketoisovalerate (KIV) | 91.65 |
| α-keto-β-methyl-n-valerate (KMV) | 6.91 |
| 2-ketoisocaproate (KIC) | 0.86 |

Example 2

Preparation of 2-ketoisovalerate (i) Cationic Ion Exchange, (ii) Anionic Ion Exchange)

A *Corynebacterium glutamicum* strain having the genotype Δ-aceE, Δ-ilvE and which overexpresses the genes ilvBN, ilvD and ilvD was cultured in shake flasks with LB media until the stationary phase was reached. The culture medium contained a carbon source and nitrogen source. The culture broth was centrifuged in order to remove cells and cell debris. The supernatant of the culture broth had a pH of 6.7 and contained 5 g/l 2-ketoisovalerate.

Then the supernatant was percolated on a strong cationic resin (Amberlite FPC 22Na) in order to remove amino acids and cations (mainly $Na^+$). For this step 350 ml resin volume was used per 1000 ml culture broth (supernatant). Then the resin was washed with 1 volume $H_2O$ and the effluent fraction was collected until a Brix of below 0.1 was reached.

The effluent having a Brix of 7 was percolated on a weak anionic resin (Amberlite IRA-67) in order to remove basic impurities. For this step 750 ml resin volume was used per 1000 ml culture broth (supernatant). Then the resin was eluted with HCl 2.7N and the effluent fractions were collected until analysis showed chlorides appearance.

Subsequently the chlorides-free fractions were pooled and $CaCO_3$ was added until pH 5.5 to 6.0 was reached. The solution was discoloured for 1 to 5 hours using 2 wt. -% active charcoal per weight 2-ketoisovalerate. Then the solution was filtered through a 0.45 μm membrane in order to remove the charcoal.

The filtrate was concentrated on a Büchi evaporator at a temperature of 40-45° C. and a pressure of 20-25 mbar until a suspension of crystals was obtained. The suspension was cooled slowly down to 20° C. and after at least 1 hour at 20° C. the crystals were filtered on a glass funnel and washed with $H_2O$.

The wet cake was dried under vacuum at a temperature of 40-45° C. until constant weight was reached and subsequently analysed as $Ca^{2+}$ salt of 2-ketoisovalerate. Analysis by HPLC revealed a purity of said 2-ketoisovalerate salt of greater than 85% by aera (see table 2).

TABLE 2

Purity of 2-ketoisovalerate obtained according to example 2

| Compound | amount [% by aera] |
| --- | --- |
| 2-ketoisovalerate (KIV) | 85.07 |
| α-keto-β-methyl-n-valerate (KMV) | 0.70 |
| 2-ketoisocaproate (KIC) | 0.65 |

Example 3

Preparation of 2-ketoisovalerate Without Ion Exchange Treatment (DSP Part)

According to examples 1 and 2 the *Corynebacterium glutamicum* strain was fermentated. Having finished the fermentation process the supernatant of the culture broth (270L, pH 2.6, containing 40 g/l 2-ketoisovalerate) was adjusted to pH 7.5 with 8.2 kg NaOH 50%, and concentrated (double-jacket reactor at 70° C., 40-50 mbar) until Brix 40 (105 g/l 2-ketoisovalerate); it was then acidified with 29.7 kg $H_2SO_4$ 30% to pH<1.0

The acidified solution was concentrated on a double-jacket reactor at a temperature of 70° C. and a pressure of 40-50 mbar. The receipts were collected until no further distillation occurred and an oily residue was obtained. The oily residue was added with 10L $H_2O$ and the concentration was continued until no more distillation occurred. This step was repeated as many times until the associated distillation receipt had an overall Brix below 0.5.

Subsequently all receipts from the distillation (230L) were pooled and 3.5 kg $CaCO_3$ were added until pH 4.5 was reached. The solution was decoloured for 1 to 5 hours using 2 wt.-% active charcoal per weight 2-ketoisovalerate. Then the solution was filtered through a filter press in order to remove the charcoal.

The filtrate was concentrated on a double-jacket reactor at a product temperature of 35-45° C. and a pressure of 40-50 mbar until a suspension of crystals was obtained. The suspension was cooled slowly down to 20° C. and after at least 1 hour at 20° C. the crystals were centrifuged and washed with $H_2O$.

The wet cake was dried under vacuum at a temperature of 40-45° C. until constant weight was reached (5.1 kg) and subsequently analysed as $Ca^{2+}$ salt of 2-ketoisovalerate. Analysis by HPLC revealed a purity of said 2-ketoisovalerate salt of greater than 99% by area (see table 1).

TABLE 1

Purity of 2-ketoisovalerate obtained according to this example

| Compound | amount [% by area] |
| --- | --- |
| 2-ketoisovalerate (KIV) | 99.7 |
| α-keto-β-methyl-n-valerate (KMV) | 0.2 |
| 2-ketoisocaproate (KIC) | 0.1 |

The invention claimed is:

1. A method for preparing a 2-keto carboxylic acid having the general formula (I) $R^1$ CO—COOH, wherein $R^1$ is a branched alkyl group having 3 to 7 carbon atoms, or a salt thereof, comprising:
   (a) producing a culture broth containing a 2-keto carboxylic acid or a salt thereof by fermenting a culture medium with a microorganism until the culture medium contains at least 15 g/l 2-ketoisovaleric acid or a salt thereof;
   (b) subjecting the culture broth obtained in (a) to one or more processes selected from the group consisting of an ion exchange process, an extraction process, and a distillation process;
   (c) subjecting the product obtained in (b) to further concentration, precipitation or crystallization or combination thereof and obtaining a 2-keto carboxylic acid or a salt thereof;
   wherein the purity of the 2-keto carboxylic acid or its salt is 60% by weight or more;
   wherein the microorganism used for the fermentation step is *Corynebacterium glutamicum*;
   wherein the *Corynebacterium glutamicum* is deficient or reduced in the proteins of transaminase B, encoded by the ilvE gene and described by E.C. 2.6.1.42, and the E1 subunit of pyruvate dehydrogenase encoded by the aceE gene and described by E.C. 1.2.4.1,
   wherein said in said *Corynebacterium glutamicum* the genes of ilvBN, which encodes acetohydroxyacid synthase described by E.C. 4.1.3.18, ilvC a gene encoding acetohydroxyacid isomeroreductase described by E.C. 1.1.1.86, and ilvD a gene encoding dihydroxyacid dehydratase described by E.C. 4.2.1.9 are overexpressed, and
   wherein the 2-keto carboxylic acid is 2-ketoisovaleric acid.

2. The method according to claim 1, comprising:
   (b) subjecting the culture broth obtained in (a) to distillation process which is accompanied by a pH-shift of the culture broth.

3. The method according to claim 1, comprising:
   (b) subjecting the culture broth obtained in (a) to ion exchange.

4. The method according to claim 1, whereby the effluent obtained in (b) is purified by at least one process selected from the group consisting of ion exchange, extraction or distillation.

5. The method according to claim 1 comprising:
   (b) subjecting the culture broth obtained in (a) to ion exchange; and
   (c) subjecting the effluent obtained in (b) to further purification comprising at least one of ion exchange, extraction or distillation; and
   (d) subjecting the product obtained in (c) to a further concentration, precipitation or crystallization step or combination thereof and obtaining 2-ketoisovaleric acid or a salt thereof.

6. The method according to claim 1, wherein the purity of the 2-ketoisovaleric acid or its salt obtained is 80% by weight or more.

7. The method according to claim 1, wherein the purity of the 2-ketoisovaleric acid or its salt obtained is 90% by weight or more.

8. The method according to claim 1, wherein the culture broth obtained in (a) contains at least 20 g/l 2-ketoisovaleric acid or a salt thereof.

9. The method according to claim 1, wherein the culture broth obtained in (a) contains at least 40 g/l 2-ketoisovaleric acid or a salt thereof.

10. The method according to claim 1, wherein before the culture broth is applied to the ion exchange (b), an additional step of removal of cells and/or cell debris from the culture broth is carried out.

11. The method according to claim 10, wherein the removal is carried out by filtration, centrifugation or sedimentation or by a combination of said methods.

12. The method according to claim 10, wherein after removal of cells and/or cell debris from the culture broth and before (b) a pre-purification is carried out by using ion exchange resin or charcoal.

13. The method according to claim 1, wherein in (b) an ion exchange is carried out by using a cationic resin.

14. The method according to claim 5 that comprises ion exchange using an anionic resin in (c).

15. The method according to claim 5 that comprises steam distillation in (c).

16. The method according to claim 15, wherein the distillation is carried out at a temperature from 10 to 100° C.

17. The method according to claim 15, wherein the distillation is carried out at a pressure from 10 to 100 mbar.

18. The method according to claim 1, wherein (c) comprises precipitating or crystallizing 2-ketoisovaleric acid as at least one salt of $Ca^{2+}$, $Mg^{2+}$, $Na^+$, or $K^+$ or as a salt of an amino acid.

19. The method according to claim 1 that comprises (a) producing a culture broth containing a 2-keto carboxylic acid or a salt thereof by fermenting a culture medium with a microorganism, wherein said microorganism is *Corynebacterium glutamicum* that can produce from said medium a culture broth having a pH of pH 2.6 or more, but less than pH 6.7.

20. The method according to claim 1, wherein (a) is performed until the culture medium has a pH of pH 2.6 or more, but less than pH 6.7.

\* \* \* \* \*